US011758888B2

United States Patent
Qiang et al.

(10) Patent No.: US 11,758,888 B2
(45) Date of Patent: Sep. 19, 2023

(54) COMBINATION OF ANTISENSE RNA SEQUENCES AND USE IN THE PRODUCTION OF TILAPIA WITH DEGENERATED SEXUAL ORGANS

(71) Applicant: Freshwater Fisheries Research Center of Chinese Academy of Fishery Sciences, Wuxi (CN)

(72) Inventors: Jun Qiang, Wuxi (CN); Zheming Cao, Wuxi (CN); Pao Xu, Wuxi (CN); Jie He, Wuxi (CN); Kai Liu, Wuxi (CN); Gangchun Xu, Wuxi (CN); Hongxia Li, Wuxi (CN); Yifan Tao, Wuxi (CN); Haojun Zhu, Wuxi (CN)

(73) Assignee: Freshwater Fisheries Research Center of Chinese Academy of Fishery Sciences, Jiangsu (CN)

( * ) Notice: Subject to any disclaimer, the term of this patent is extended or adjusted under 35 U.S.C. 154(b) by 0 days.

(21) Appl. No.: 17/092,906

(22) Filed: Nov. 9, 2020

(65) Prior Publication Data
US 2022/0071182 A1 Mar. 10, 2022

(30) Foreign Application Priority Data

Sep. 4, 2020 (CN) .......................... 202010920690.8

(51) Int. Cl.
*A01K 67/027* (2006.01)
*C12N 15/113* (2010.01)

(52) U.S. Cl.
CPC .......... *A01K 67/027* (2013.01); *C12N 15/113* (2013.01); *A01K 2227/40* (2013.01)

(58) Field of Classification Search
None
See application file for complete search history.

(56) References Cited

FOREIGN PATENT DOCUMENTS

WO WO-2014096428 A1 * 6/2014 ............... A01H 1/00

OTHER PUBLICATIONS

Schimmer BP, White PC. Minireview: steroidogenic factor 1: its roles in differentiation, development, and disease. Mol Endocrinol. Jul. 2010;24(7):1322-37. doi: 10.1210/me.2009-0519. Epub Mar. 4, 2010. PMID: 20203099; PMCID: PMC5417463. (Year: 2010).*

* cited by examiner

*Primary Examiner* — Allison M Fox
*Assistant Examiner* — Alyssa G Weston
(74) *Attorney, Agent, or Firm* — Thomas | Horstemeyer, LLP (57) ABSTRACT

The present disclosure provides a combination of antisense RNA sequences and use thereof in the production of tilapia with degenerated sexual organs, belonging to the technical field of molecular biology and reproductive biology, the combination of antisense RNA sequences includes antisense RNA of steroidogenic factors SF1-1 and SF1-2; the nucleotide sequences of Anti-SF1-1-I, Anti-SF1-1-II, Anti-SF1-2-I and Anti-SF1-2-II are set forth in SEQ ID NO:1-SEQ ID NO:4 respectively. The method of the present disclosure introduces antisense RNA fragments into the eggs through the fertilization hole to realize effective and accurate targeted intervention for regulating the gene expression, and the method has the advantages of simple operation, minimal egg damage, high success rate, stable phenotype after breeding, and excellent application prospects.

9 Claims, 5 Drawing Sheets
Specification includes a Sequence Listing.

COMBINATION OF ANTISENSE RNA SEQUENCES AND USE IN THE PRODUCTION OF TILAPIA WITH DEGENERATED SEXUAL ORGANS

CROSS REFERENCE TO RELATED APPLICATION

This disclosure claims the priority of Chinese Patent Application No. 202010920690.8 entitled "Combination of antisense RNA sequences and use thereof in the production of tilapia with degenerated sexual organs" filed with China National Intellectual Property Administration on Sep. 4, 2020, which is incorporated herein by reference in its entirety.

SEQUENCE LISTING

This application contains a sequence listing filed in ST.25 format entitled "SEQUENCE_LISTING. TXT" filed on Nov. 9, 2020, having 2854 bytes. The content of the sequence listing is incorporated herein in its entirety.

TECHNICAL FIELD

The present disclosure belongs to the technical field of molecular biology and reproductive biology, especially relating to a combination of antisense RNA sequences and use thereof in the production of tilapia with degenerated sexual organs.

BACKGROUND ART

Tilapia nilotica (*Oreochromis niloticus*) is one of the main cultured freshwater fishes in the world, characterized with fast growth and strong fecundity, and mainly manifested as early sexual maturity. Female fish cannot eat during the breeding season and need to consume a large number of energy for breeding needs. Meanwhile, too many small fish may compete with female fish for feeding, which seriously affects the growth of adult fish. Therefore, there is an urgent need to breed all male tilapia in production. At present, there are three main methods for breeding all male tilapia: a. Cross breeding method, which mainly uses the chromosomal differences between *Oreochromis niloticus* and *Orechromis aureus* to achieve cross breeding, and the male rate of offspring may reach up to 85%-97%. However, this method has extremely high requirements for parent breeding, causing the parents have the characteristics of low spawning rate, low emergence rate and slow growth rate. b. Male transformation induced by high temperature: raising the water temperature to help increasing the male rate of tilapia. When the water temperature is higher than 34° C., the male rate can reach up to 80%, while the deformity rate exceeds 15%. c. Male transformation by hormone: it is the main method currently in use, in which the sex reversal is carried out by adding methyltestosterone to the feed. However, hormones easily remain in fish, causing excessive drug residues. At the same time, the excessive methyltestosterone may be discharged into water or ingested by the human body, thereby endangering human health.

At present, there is still no safe and effective method to abort tilapia.

SUMMARY OF THE INVENTION

In view of the above, the purpose of the disclosure is to provide a combination of antisense RNA sequences and use thereof in the production of tilapia with degenerated sexual organs.

Antisense RNA refers to RNA that may directly inhibit the expression of related genes after being complementary to mRNA. It blocks gene expression and has the characteristic of strong specificity and simple operation. Meanwhile, low-abundance antisense RNA can also produce high-efficiency inhibition; antisense RNA cannot be translated to produce protein, and does not destroy the endogenous gene structure, so it has great safety.

Steroidogenic factor 1 (SF1) is an important transcription factor that is essential for steroid producing regulation, gonadal development, sex determination and differentiation. The double antisense RNA is used to inhibit the expression level of steroidogenic factor 1 protein, and to interfere with hormone secretion and gonadal development in the disclosure, thereby obtaining tilapia with degenerated sexual organs.

In order to achieve the purpose of the disclosure, the following technical schemes are provided:

The present disclosure provides a combination of antisense RNA sequences, including antisense RNA of steroidogenic factors SF1-1 and SF1-2.

In some embodiments, the antisense RNA of steroidogenic factor SF1-1 includes an Anti-SF1-1-I and an Anti-SF-1-1-II; the antisense RNA of steroidogenic factor SF1-2 includes an Anti-SF1-2-I and an Anti-SF1-2-II; the nucleotide sequences of Anti-SF1-1-I, Anti-SF1-1-II, Anti-SF1-2-I and Anti-SF1-2-II are set forth in SEQ ID NO:1-SEQ ID NO:4 respectively.

The present disclosure also provides a use of the combination of antisense RNA sequences in the production of tilapia with degenerated sexual organs.

In some embodiments, the use includes the steps of:

1) cloning the Anti-SF1-1-I, Anti-SF1-1-II, Anti-SF1-2-I and Anti-SF1-2-II into an expression vector to obtain a first recombinant vector, a second recombinant vector, a third recombination vector and a fourth recombination vector;

2) using the first recombination vector, the second recombination vector, the third recombination vector, and the fourth recombination vector as templates respectively, and performing PCR amplification with specific primers to obtain four amplified products;

3) after mixing the four amplified products obtained above with a cationic liposome and a spermatozoa preservative fluid respectively, equilibrating at 15-30° C. for 20-40 min to obtain a transfection reagent;

4) mixing the transfection reagent with eggs for transfection to obtain transfected eggs;

5) mixing the transfected eggs with sperms for fertilization and hatching to obtain tilapia fries with degenerated sexual organs.

In some embodiments, the expression vector in step 1) is a pcDNA3.1 expression vector, and a cloning site is located between the Xho I and Xba I restriction sites.

In some embodiments, the specific primers in step 2) include PolyAF2 and PolyAR1, and the nucleotide sequences of the PolyAF2 and PolyAR1 are set forth in SEQ ID NO: 5 and SEQ ID NO: 6.

In some embodiments, the volume ratio of the four amplified products in step 3) is (0.5-1.5):(0.5-1.5):(0.5-1.5): (0.5-1.5); the volume ratio of the total volume contained the four amplified products, the cationic liposome and the spermatozoa preservative fluid is 4:4:(60-65).

In some embodiments, the spermatozoa preservative fluid takes water as a solvent and includes the following components: 3%-5% sucrose in mass fraction, 2%-4% glycerol in volume fraction, and 0.5%-1.5% DMSO in volume fraction.

In some embodiments, a solution for promoting the opening of fertilization hole is added to the eggs in step 4). The solution for promoting the opening of fertilization hole takes water as a solvent and includes the following components: sodium chloride 5-7 g/L, potassium chloride 0.05-0.15 g/L, calcium chloride 0.05-0.15 g/L, sodium bicarbonate 0.05-0.15 g/L, sodium dihydrogen phosphate 0.05-0.15 g/L and glucose 1.0-1.5 g/L.

In some embodiments, 1.5 mL of the solution for promoting the opening of fertilization hole and 0.8 mL of transfection reagent are added to every 120 to 150 eggs.

Beneficial effects of the present disclosure: the combination of antisense RNA sequences provided by the present disclosure can accurately inhibit the splicing and translation of intron and exon at the 5'-end of the steroidogenic factor 1, so that the nucleus cannot correctly identify the mRNA, thereby affecting protein translation thereof; the expression of target genes related to the hypothalamic-pituitary-gonadal axis and the secretion of sex hormones are interfered by inhibiting the protein translation of steroidogenic factor 1, which causes degeneration of the sexual organs on female and male fish. The method of the present disclosure introduces antisense RNA fragments into the eggs through the fertilization hole to realize effective and accurate targeted intervention for regulating the gene expression, and the method has the advantages of simple operation, minimal egg damage, high success rate, stable phenotype after breeding and excellent application prospects.

DETAILED DESCRIPTION OF THE EMBODIMENTS

The present disclosure provides a combination of antisense RNA sequences, including antisense RNA of steroidogenic factors SF1-1 and SF1-2.

In the present disclosure, the antisense RNA of steroidogenic factor SF1-1 includes Anti-SF1-1-I and Anti-SF1-1-I; the antisense RNA of steroidogenic factor SF1-2 includes Anti-SF1-2-I and Anti-SF1-2-II; the nucleotide sequences of Anti-SF1-1-I, Anti-SF1-1-II, Anti-SF1-2-I and Anti-SF1-2-II are preferably set forth in SEQ ID NO:1-SEQ ID NO:4 respectively; specifically as follows:

Anti-SF1-1-I:
CATCTGGTTCAGTCACTTTGCGTAAGCTGACGTCGTTCATGAACCTACAG

ACACATACGGCGGTTGAGTGATTTATTATCCTGCGATATGTTTACTTTTA

GATTTTTATTTTT.

Anti-SF1-1-II:
AATAACTGACAAACTATTCTTAACAATGAAATGTGTTTATAGTTTGTTGT

TGTGGTTTTGTTGCTTTCACCTGATCTGACTCGCTGCTGAGTCTCATCTG

GTTC.

Anti-SF1-2-I:
TGCTGTCTATATCGGGGATGCTTTAGGAGCCAGAAGGGCCAATAGAAAGT

GTAGTACGATGATGACCATTCAAGAGCTCAGAGTGAAACTCCTTTCCTTC

GC.

Anti-SF1-2-II:
AGGAAAACGGAGGCACTTACCGTGAGCCTTGTCTCCCAACATTTGAGCAG

CAGACAGCAGGCAGGCAGTGATGATTGTCTGATGATTAAAACCTGGATGT

AG.

Figure 1:
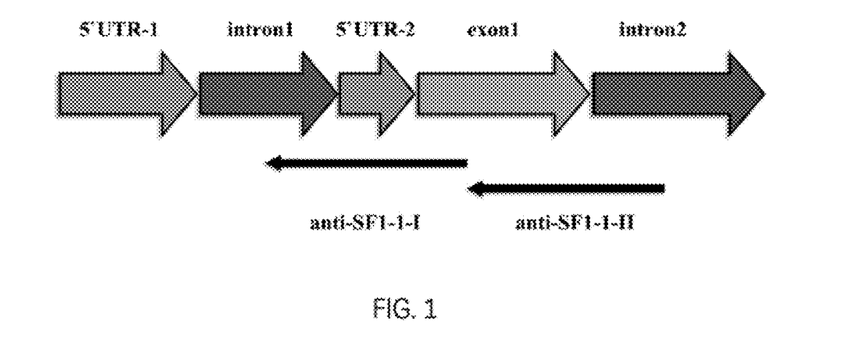
FIG. 1 shows a schematic sequence design of Anti-SF1-1 double antisense RNA.
Figure 2:
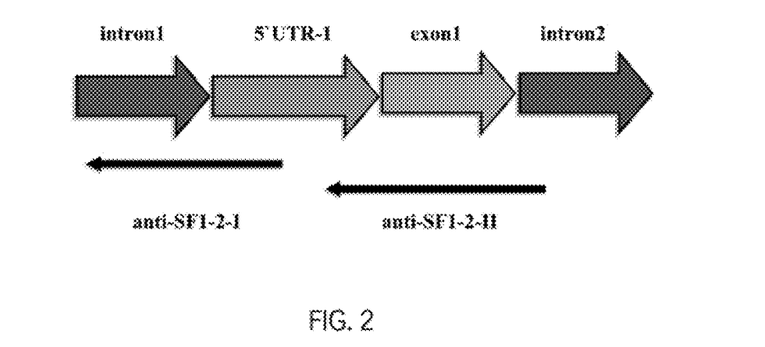
FIG. 2 shows a schematic sequence design of Anti-SF1-2 double antisense RNA.

In the present disclosure, the schematic sequence design of the Anti-SF1-1 double antisense RNA is shown in FIG. 1; the schematic sequence design of the Anti-SF1-2 double antisense RNA is shown in FIG. 2.

The present disclosure also provides a use of the combination of antisense RNA sequences in the production of tilapia with degenerated sexual organs.

The use of the present disclosure preferably comprises the following steps: 1) cloning the Anti-SF1-1-I, Anti-SF1-1-II, Anti-SF1-2-I and Anti-SF1-2-II into expression vectors to obtain recombinant vectors; 2) using the recombination vectors as templates, and performing PCR amplification with specific primers to obtain four amplified products; 3) after mixing the four amplified products with a cationic liposome and a spermatozoa preservative fluid respectively, equilibrating at 15-30° C. for 20-40 min to obtain transfection reagents; 4) mixing the transfection reagents with the eggs for transfection to obtain transfected eggs; 5) mixing the transfected eggs with sperms for fertilization and hatching to obtain tilapia fries with degenerated sexual organs.

In some embodiments, the Anti-SF1-1-I, Anti-SF1-1-II, Anti-SF1-2-I and Anti-SF1-2-II are respectively cloned into expression vectors to obtain recombinant vectors. In some embodiments, the Anti-SF1-1-I, Anti-SF1-1-II, Anti-SF1-2-I and Anti-SF1-2-II are preferably obtained by artificial synthesis. In some embodiments, the expression vector is preferably a pcDNA3.1 expression vector, and the cloning site is preferably located between the Xho I and Xba I restriction sites; the recombinant vector contains a CMV promoter for efficient expression. In some embodiments, there is no particular limitation on the specific cloning method, a conventional cloning method in the field will do.

In some embodiments, the recombinant vectors are used as templates and PCR amplification is performed with specific primers to obtain four amplified products after obtaining the recombinant vectors. In some embodiments, the specific primers include PolyAF2 and PolyAR1, of which the nucleotide sequences are set forth in SEQ ID NO: 5 and SEQ ID NO: 6, specifically are as follows: PolyAF2: TTTTGCGCTGCTTCGCGATGTAC; polyAR1: TCCC-CAATCCTCCCCCTTGCTG. In some embodiments, the 50 μL PCR amplification system contains 25 μL of 2×master-mix, 2.5 μL of primers PolyAF2 and PolyAR1 respectively, 18 μL of ultrapure water and 2 μL of amplified products. The PCR amplification procedure is as follows: pre-denaturing at 95° C. for 2 min, (denaturing at 95° C. for 30 s, annealing at 50° C. for 30 s, extending at 72° C. for 2 min), 34 cycles, extending at 72° C. for 5 min. The amplified product of the disclosure contains the sequence from the CMV enhancer to the downstream of tailing sequence.

In some embodiments, after obtaining the amplified products, the four obtained amplified products, cationic liposome, and spermatozoa preservative fluid are mixed and then equilibrated at 15-30° C. for 20-40 min to obtain transfected agents. In some embodiments, the volume ratio of the four amplified products is preferably (0.5-1.5):(0.5-1.5):(0.5-1.5):(0.5-1.5), more preferably (0.8-1.2):(0.8-1.2):(0.8-1.2):(0.8-1.2). The volume ratio of the total volume containing the four amplificated products, the cationic liposome and the spermatozoa preservative fluid is preferably 4:4:(60-65), more preferably 4:4:(61-64), further preferably 4:4:62. In an embodiment, the cationic liposome is Lipofecter; the spermatozoa preservative fluid takes water as a solvent, and preferably includes the following components: 3%-5% sucrose in mass fraction, 2%-4% glycerol in volume fraction, and 0.5%-1.5% DMSO in volume fraction, and more preferably includes 4% sucrose, 3% glycerol, and 1.0% DMSO. In an embodiment, the four amplified products are mixed first, and then the mixture is mixed with the cationic liposome and the spermatozoa preservative fluid. In some embodiments, the equilibrating is preferably conducted for 25-35 min, more preferably for 30 min.

In some embodiments, the transfection reagents are mixed with the eggs for transfecting to obtain the transfected eggs. In the present disclosure, it is preferable that a solution for promoting the opening of fertilization hole is added to the eggs. The solution for promoting the opening of fertilization hole takes water as a solvent, and preferably includes the following components: sodium chloride 5-7 g/L, potassium chloride 0.05-0.15 g/L, calcium chloride 0.05-0.15 g/L, sodium bicarbonate 0.05-0.15 g/L, sodium dihydrogen phosphate 0.05-0.15 g/L and glucose 1.0-1.5 g/L, more preferably includes sodium chloride 6 g/L, potassium chloride 0.1 g/L, calcium chloride 0.1 g/L, sodium bicarbonate 0.1 g/L, sodium dihydrogen phosphate 0.1 g/L, and glucose 1.2 g/L. In some embodiments, the solution for promoting the opening of fertilization hole is able to prolong the opening time of fertilization hole, ensure the full entry of antisense RNA fragments. In some embodiments, it is preferable that 1.5 mL of the solution for promoting the opening of fertilization hole and 0.8 mL of transfection reagent are added to every 120 to 150 eggs. In some embodiments, for the female tilapia with mature eggs and gonads, the mature standard of the gonads is preferably that the gonads are salient, ruddy and slightly open; in some embodiments, the method for collecting eggs is preferably as follows: wiping the water off the surface of the fish and surrounding of the genitals, squeezing the abdomen to squeeze out the mature eggs; in an embodiment, the mature eggs are placed in a stainless steel basin. In some embodiments, the step of mixing the transfection reagent with the eggs is preferably conducted for 10-20 min, more preferably for 15 min; the mixing is preferably carried out in a stainless steel basin, and it is preferable to perform slight shaking during the mixing process to promote the antisense RNA to enter the eggs.

In some embodiments, after obtaining the transfected eggs, the transfected eggs and the sperms are mixed, fertilized and hatched to obtain the tilapia fries with degenerated sexual organs. In some embodiments, the ratio of the transfected eggs to sperms is preferably 120-150 eggs per 0.2 mL sperms. In some embodiments, the goose feathers are preferably used to stir for 30 seconds after the transfected eggs and sperms are mixed, then the incubation water is added to complete the artificial insemination. In the present disclosure, the volume of incubation water for 120-150 eggs is preferably 1.5-2.5 mL, more preferably 2 mL. In some embodiments, the hatching is carried out in a hatching jar, and the hatching temperature is preferably 28.5-29.5° C., more preferably 29° C.; the water flow rate of the hatching is preferably 4-6 L/min, more preferably 5 L/min, the water flow rate can ensure the fertilized eggs to roll fully, and the hatching is preferably carried out for 92~108 h.

The technical solutions provided by the disclosure will be described in detail below with reference to examples, but they should not be understood as any limitation to the scope of the present disclosure.

Example 1

Step 1: Design of the first antisense RNA sequence of SF1-1 (Anti-SF1-1-I):

(SEQ ID NO: 1)
CATCTGGTTCAGTCACTTTGCGTAAGCTGACGTCGTTCATGAACCTACAG

ACACATACGGCGGTTGAGTGATTTATTATCCTGCGATATGTTTACTTTTA

GATTTTTATTTTT.

The antisense RNA comprised a first intron partial sequence, a first exon partial sequence and a 5-terminal non-translated sequence of four bases. The design purpose was to interfere with the post-transcriptional processing of the SF1-1 gene and the translation initiation of the mRNA of this gene.

Design of the second antisense RNA sequence (Anti-SF1-1-II):

(SEQ ID NO: 2)
AATAACTGACAAACTATTCTTAACAATGAAATGTGTTTATAGTTTGTTGT

TGTGGTTTTGTTGCTTTCACCTGATCTGACTCGCTGCTGAGTCTCATCTG

GTTC.

The antisense RNA comprised a second intron partial sequence and a first exon partial sequence. The design purpose was to interfere with the post-transcriptional processing of the SF1-1 gene.

Step 2: Design of the first antisense RNA sequence of SF1-2 (Anti-SF1-2-I):

(SEQ ID NO: 3)
TGCTGTCTATATCGGGGATGCTTTAGGAGCCAGAAGGGCCAATAGAAAGT

GTAGTACGATGATGACCATTCAAGAGCTCAGAGTGAAACTCCTTTCCTTC

GC.

The antisense RNA comprised a first intron partial sequence and a 5-terminal non-translated sequence of eighty bases. The design purpose was to interfere with the post-transcriptional processing of the SF1-2 gene and the translation initiation of the mRNA of this gene.

Design of the second antisense RNA sequence of SF1-2 (Anti-SF1-2-II):

(SEQ ID NO: 4)
AGGAAAACGGAGGCACTTACCGTGAGCCTTGTCTCCCAACATTTGAGCAG

CAGACAGCAGGCAGGCAGTGATGATTGTCTGATGATTAAAACCTGGATGT

AG.

The antisense RNA comprised a second intron partial sequence, a first exon sequence and a 5-terminal non-translated sequence of sixty bases. The design purpose was to interfere the translation initiation of the SF1-2 gene.

Step 3: PCR Amplification

The four antisense RNA sequences were cloned into the site between the Xho I and Xba I in the pcDNA3.1 expression vector (containing the CMV promoter for high efficient expression) after the four antisense RNA sequences were synthesized, and the cloning product was used as a template for subsequent PCR amplification. A pair of specific primers was designed to amplify the template respectively: PolyAF2: TTTGCGCTGCTTCGCGATGTAC (SEQ ID NO: 5); the reverse primer polyAR1: TCCC-CAATCCTCCCCCTTGCTG (SEQ ID NO: 6). The 50 µL reaction system contained 25 µL of 2×mastermix, 2.5 µL of primers PolyAF2 and PolyAR1 respectively, 18 µL of ultrapure water and 2 µL of template. The PCR amplification procedure is as follows: pre-denaturing at 95° C. for 2 min, (denaturing at 95° C. for 30 s, annealing at 50° C. for 30 s, extending at 72° C. for 2 min), 34 cycles, extending at 72° C. for 5 min. The amplified product contained the sequence from the CMV enhancer to the downstream of tailing sequence. In negative control group, the blank expression vector was amplified according to the above PCR procedure, the reaction system was 50 µL, containing 25 µL of 2×mastermix, 2.5 µL of primers PolyAF2 and PolyAR1 respectively, and 20 µL of ultrapure water.

Step 4: Transfection reagent preparation: the PCR amplified products (the PCR amplified products of each group obtained in step 3 was mixed in a volume ratio of 1:1:1:1), blank expression vector amplified products (negative control group) or ultrapure water (control group), cationic liposome Lipofecter, spermatozoa preservative fluid (4% sucrose, 3% glycerol and 1% DMSO) were mixed at a ratio of 4 µL:4 µL:62 µL, and the mixture was equilibrated at room temperature for 30 min.

Step 5: Female fish selection: 1 female tilapia with mature gonads (the gonads were salient, ruddy and slightly open) was chosen. The water on the surface of the fish and around the genitals was gently wiped off with a dry towel. The abdomen was gently squeezed to squeeze out the mature eggs, and the eggs were placed in 3 clean and dry stainless steel basins respectively. The number of eggs in each stainless steel basin was 120-150. The experiments were divided into 3 groups: a control group (without any addition); a negative control group (transfected with blank plasmid) and an experimental group (transfected with target templates).

Step 6: Introduction of antisense RNA fragments: First, 1.5 mL solution for promoting the opening of fertilization hole (each liter of water contained 6 g of sodium chloride, 0.1 g of potassium chloride, 0.1 g of calcium chloride, and 0.1 g of sodium bicarbonate, 0.1 g of sodium dihydrogen phosphate and 1.2 g of glucose) was added respectively into the stainless steel basin where the eggs were placed. The opening time of the egg fertilization hole could be prolonged and the antisense RNA fragments could be fully introduced by using the chemical solution that obtained above. Then 0.8 mL of transfection reagent was added. The stainless steel basin was gently shaken for 15 min to make the antisense RNA fragment enter the eggs through the fertilization hole. In negative control group, 0.8 mL of transfection reagent containing blank plasmid was added according to the above operation. In control group, 0.8 mL of transfection reagent containing ultrapure water was added according to the above operation.

Step 7: Male fish selection: 1 male fish with well-developed gonads (the genital pores were ruddy and salient) was chosen, 0.2 mL of semen was gently sucked and placed into the stainless steel basin mentioned above with a disposable dropper. The mixed solution containing sperm was stirred for 30 s by using goose feathers, 2 mL of incubation water was added to complete the artificial insemination process.

Step 8: Artificial hatching: The fertilized eggs were placed in 3 hatching jars respectively, with water temperature of 29° (C and water flow rate of 5 L/min to ensure that the fertilized eggs could roll fully. A large number of fish fries could be hatched after 92 h.

The newly-hatched larvae were placed and fed in a small water circulating system for 30 days, then the feeding larvae were transferred to a large water circulating system for culturing. The culture cycle was a 150-day period. The fish were stopped feeding for 1 day before the end of the experiment, and then the body shape of the fish, sexual organs, and gonads were photographed. The blood was drawn from tail vein to extract serum for hormone determination, and gonadal weight was weighed. At the same time, gonadal tissues were selected for FIE staining, related gene quantification and protein level determination.

TABLE 1

Terminal body weight and gonadal weight of male fish in each experimental group

| measurement index | control group | negative control group | experimental group |
|---|---|---|---|
| body weight (g) | 244.28 | 251.16 | 357.92 |
| gonadal weight (g) | 2.36 | 2.41 | 0.51 |
| gonad index | 0.975 | 0.969 | 0.143 | gonad index=[gonadal weight/(body weight−gonadal weight)]×100)

TABLE 2

The final body weight and gonadal weight of female fish in each experimental

| measurement index | control group | negative control group | experimental group |
|---|---|---|---|
| body weight (g) | 225.84 | 221.33 | 301.96 |
| gonadal weight (g) | 5.30 | 5.48 | 3.21 |
| gonad index | 2.403 | 2.539 | 1.073 |

Figure 3:
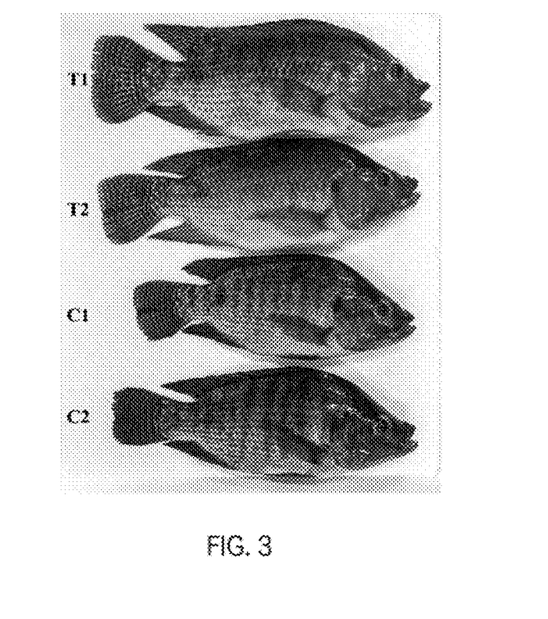
FIG. 3 is a photograph of the appearance of female fish and male fish in experimental group and control group, wherein T1 is the male Genetic Improvement of Farmed Tilapia (GIFT) in experimental group; T2 is the female GIFT in experimental group; C1 is the female GIFT in control group; C2 is the male GIFT in control group.

It can be seen from FIG. 3 that the body weight of the male and female GIFT in experimental group is significantly higher than those in control group after using antisense RNA to interfere with the expression of steroidogenic factor 1 of GIFT. However, the testis weight and gonadal index of male fish in experimental group are significantly lower than those in control and negative control groups ($P<0.01$); the ovarian weight and gonadal index of the female fish in experimental group are also significantly lower than those in control and negative control groups ($P<0.05$).

Figure 4:
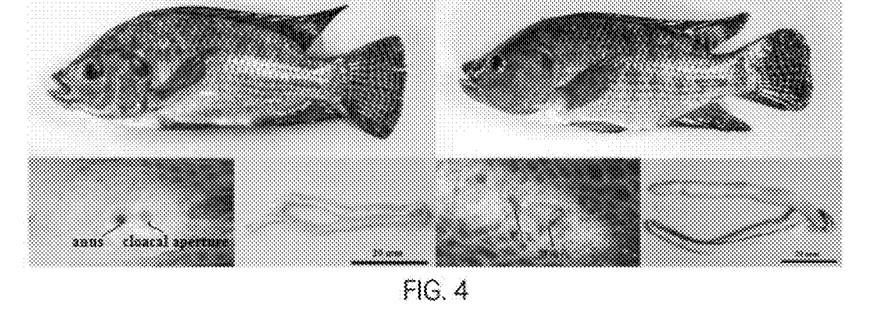
FIG. 4 shows photographs of the genital pore and gonads of male fish in experimental group and control group, in which the upper left photograph shows the male fish in experimental group, the lower left two photographs show the genital pore and gonads of the male fish in experimental group (from left to right), while the upper right photograph shows the male fish in control group, the lower right two photographs show the genital pore and gonads of the male fish in control group (from left to right).

It can be seen from FIG. 4 that the male GIFT with antisense RNA interference have almost no primary sexual characteristics after 150 days of culture; however, the sexual organs of male fish in control group are salient, ruddy and well developed.

Figure 5:
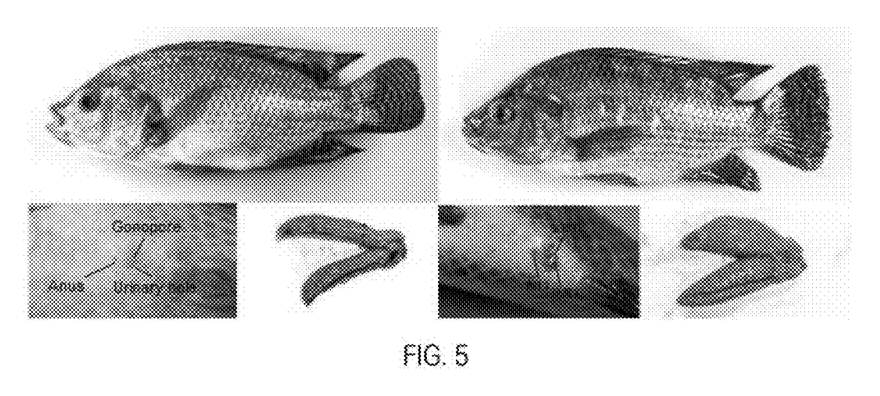
FIG. 5 shows photographs of the genital pore and gonads of female fish in experimental group and the control group, in which the upper left photograph shows the female fish in experimental group, the lower left two photographs show the genital pore and gonads of the female fish in experimental group (from left to right), and the upper right photograph shows the female fish in control group, the lower right two photographs show the genital pore and gonads of the female fish in control group (from left to right).

It can be seen from FIG. 5 that the female GIFT with antisense RNA interference have almost no primary sexual characteristics after 150 days of culture; however, the sexual organs of female fish in control group are salient, ruddy and well developed.

Determination of SF1 Gene Expression Level

The total RNA of gonadal tissue was extracted by using TRIzol kit. The cDNA was synthesized with reference to the corresponding PrimeScript™ RT Master Mix reverse transcription kit instructions, and the gene expression was detected through SYBR Premix Ex Taq kits operation steps. The relative expression level of the gene was calculated by using 18S rRNA as an internal reference. The expression level of related genes mRNA was detected by using ABI QuantStudio 5 Real-Time PCR System. The primer design was shown in Table 3. The 20 μL of reaction system contained: 0.6 μL of upstream and downstream primers (10 mmol/μL) respectively, 1 μL of cDNA, 10 μL of 2×SYBR Premix Ex Taq™ II, sterilized double distilled water added to 20 μL. The reaction program was: 95° C. for 5 min, then (95° C. for 15 s, 60° C. for 60 s) for 40 cycles, the dissolution curve program after the reaction was: 95° C. for 15 s, 60° C. for 15 s, 95° C. for 15 s. Each reaction included three replicates, and each test sample contained a negative control without template to eliminate false positive results.

TABLE 3

Primer sequence

| gene name | primer sequence (5'-3') | | |
|---|---|---|---|
| SF1-1 | F: 5'-TGTGCTCACCGGTAGTTTGG-3' | (SEQ ID NO: 7) |
| | R: 3'-ATGGGCAGCTCTGTGGAATG-5' | (SEQ ID NO: 8) |
| SF1-2 | F: 5'-GAGCGAAGGAAAGGAGTTTC-3' | (SEQ ID NO: 9) |
| | R: 5'-TGACTCGCTGCTGAGTCTCA-3' | (SEQ ID NO: 10) |
| 18S rRNA | F: 5'-GGCCGTTCTTAGTTGGTGGA-3' | (SEQ ID NO: 11) |
| | R: 5'-TTGCTCAATCTCGTGTGGCT-3' | (SEQ ID NO: 12) |

Figure 6:
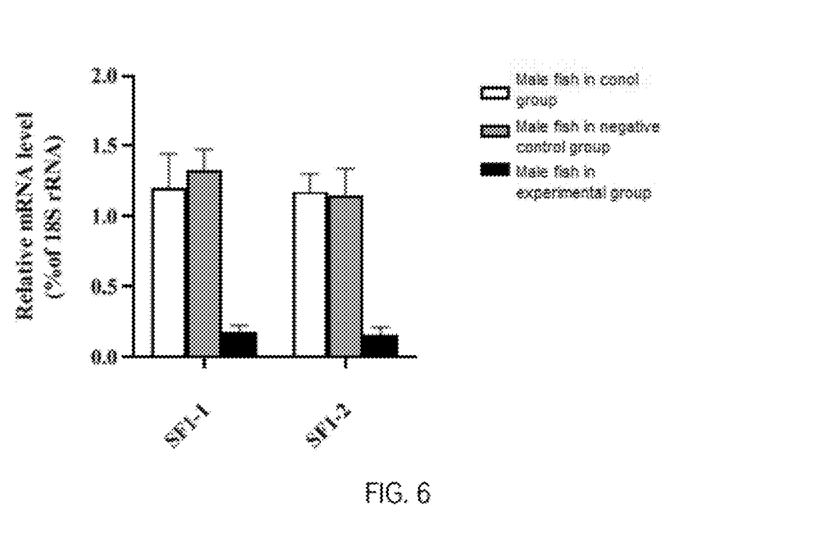
FIG. 6 shows the expression levels of male fish steroidogenic factor 1 in control group, negative control group and experimental group.

It can be seen from FIG. 6 that the expression levels of steroidogenic factor 1 type I and type II genes of the male fish in experimental group are significantly lower than those in control and negative control groups ($P<0.01$), indicating that antisense RNA inhibits mRNA transcription level of steroidogenic factor 1.

Figure 7:
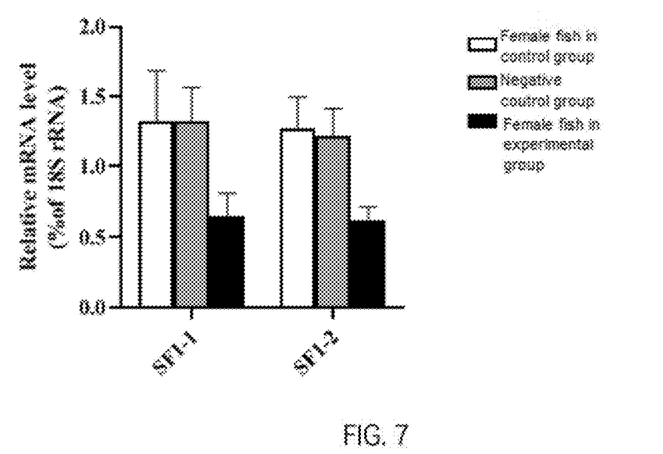
FIG. 7 shows the expression levels of female fish steroidogenic factor 1 in control group, negative control group and experimental group.

It can be seen from FIG. 7 that the expression levels of steroidogenic factor 1 type I and type II genes of the female fish in experimental group are significantly lower than those in control and negative control groups ($P<0.01$), indicating that antisense RNA inhibits mRNA transcription level of steroidogenic factor 1.

Determination of Hormone Levels in Serum

Serum testosterone of male fish, serum gonadotropin-releasing hormone of female fish, luteinizing hormone, progesterone and estradiol were determined with an ELISA kit which was purchased from Shanghai Haoben Biotechnology Co., Ltd. The concentration of hormones in serum was determined according to the kit instructions, and each sample was repeated three times. First, the standard products in the kit were diluted according to the gradient of 16:8:4:2:1 to prepare standards of different concentrations for drawing the standard curve. 40 μL of the serum to be tested was taken and determined according to the operation procedures of the kit. The experimental results were read by a multiskan spectrum microplate spectrophotometer (Bio Tek Eon). Different hormone concentrations of samples in each group were determined at different wavelengths, and the corresponding sample concentrations were calculated according to the linear regression equation of the standard curve.

TABLE 4

Comparison of hormone levels in serum of male fish in each experimental group

| measurement index | control group | negative control group | experimental group |
|---|---|---|---|
| testosterone (nmol/L) | 40.84 | 42.67 | 29.14 |

TABLE 5

Comparison of hormone levels in serum of female fish in each experimental

| measurement index | control group | negative control group | experimental group |
|---|---|---|---|
| estradiol (ng/L) | 103.29 | 112.01 | 66.43 |
| luteinizing hormone (ng/L) | 3.57 | 3.77 | 3.01 |
| gonadotropin-releasing hormone (ng/L) | 287.92 | 281.94 | 183.73 |
| progesterone (ng/ml) | 9.77 | 9.13 | 6.72 |

It can be seen from Table 4 and Table 5 that the testosterone level in serum of male fish in experimental group is significantly lower than those in control and negative control groups (P<0.05) after the steroidogenic factor 1 is inhibited by using antisense RNA; meanwhile, estradiol, gonadotropin-releasing hormone, and progesterone in serum of female GIFT in experimental group are significantly lower than those in control group (P<0.05), and the luteinizing hormone in experimental group is also lower than those in control group.

HE staining of gonadal tissue: The fixed gonadal tissues were cut into paraffin sections conventionally with a thickness of 5-6 μm and HE staining. The paraffin sections were sealed with neutral gum, and then the sections were observed and photographed under a microscope (Nikon DS-Ril).

Figure 8:
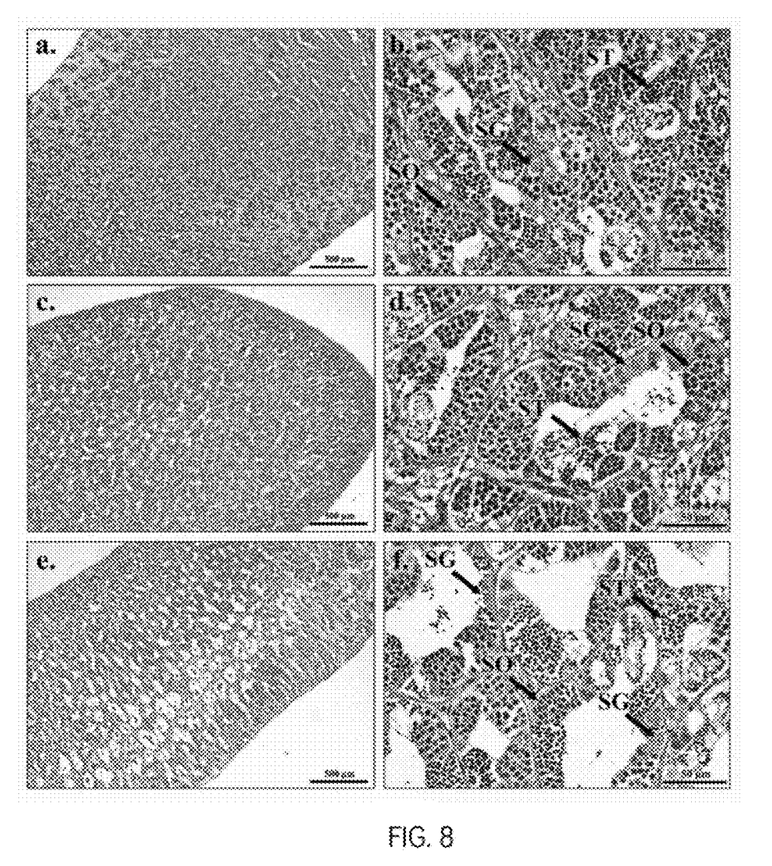
FIG. 8 shows the HE staining pictures of testis tissue development in each experimental group, wherein SG: spermatogonia; SO: spermatocytes; ST: spermatid; a: the testis of male fish in control group (40×); b: the testis of male fish in control group (400×); c: the testis of male fish in negative control group (40×); d: the testis of male fish in negative control group (400×); e: the testis of male fish in experimental group (40×); f: the testis of male fish in experimental group (400×).

It can be seen from FIG. 8 that the testis in control group shows a slender greyish white line shape and begins to enter the mature stage. The germ cells of each stage are easy to distinguish because they have different shades of hematoxylin. A large number of spermatogonia, spermatocyte and spermatid are clearly visible in control group, and dense sperms begin to appear. However, the number of spermatogonia in experimental group that inhibits the expression of steroid factor protein is significantly decreased, the number of cavities is significantly increased, the number of spermatids is significantly decreased, the number of sperm is less, and the development of testis in experimental group is significantly slow.

Figure 9:
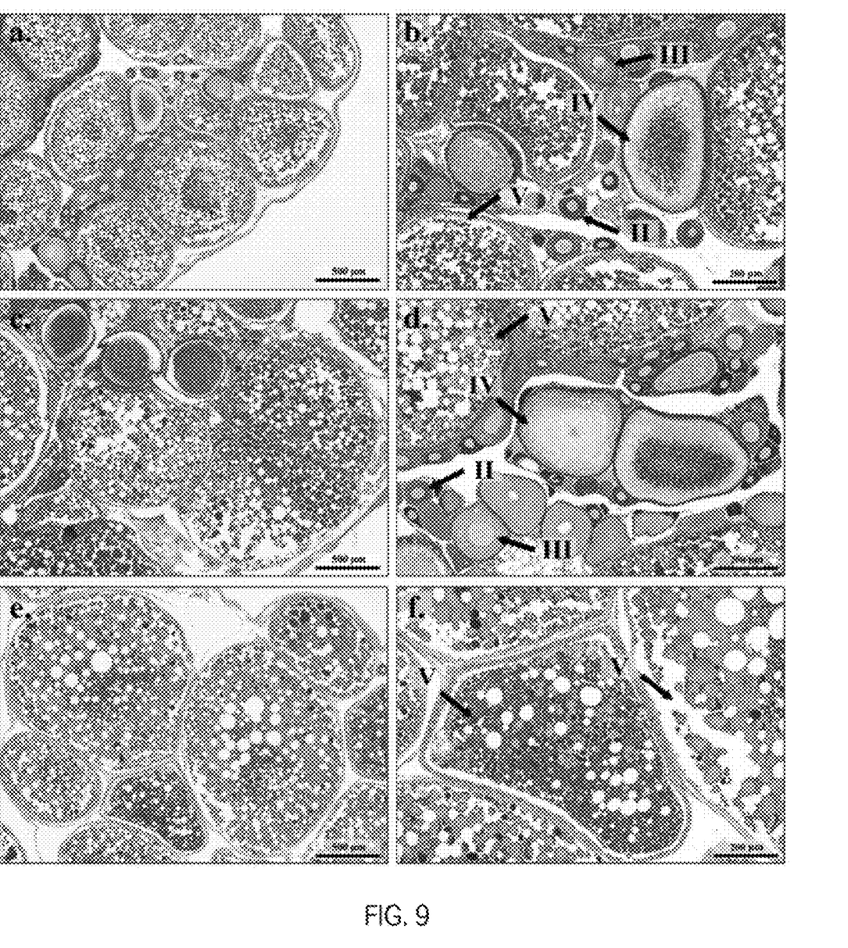
FIG. 9 shows the HE staining pictures of ovarian tissue development in each experimental group, wherein II, III, IV and V stand for oocytes in each stages; a: the ovary of female fish in control group (40×); b: the ovary of female fish in control group (400×); c: the ovary of female fish in negative control group (40×); d: the ovary of female fish in negative control group (400×); e: the ovary of female fish in experimental group (40×); f: the ovary of female fish in experimental group (400×).
Figure 10:
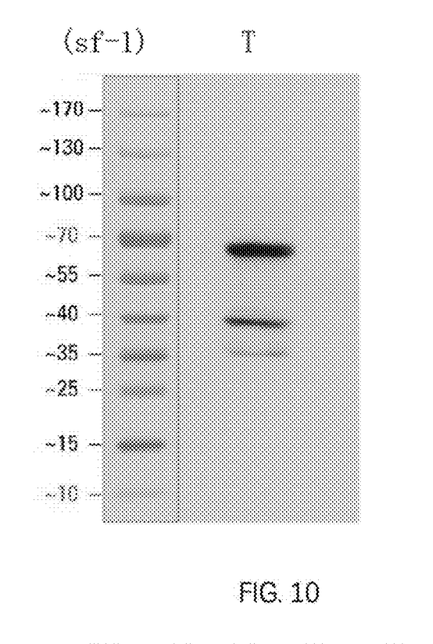
FIG. 10 shows the protein molecular weight of steroidogenic factor 1 in tilapia gonadal tissue.

It can be seen from FIG. 9 that oocytes of each stages (stages II, III, IV and V) are clearly visible in the ovarian tissue in control group, which is related to the asynchronous development of the tilapia ovary. The development of oocytes on stage II starts once the oocytes on stage V are excreted from the body. However, it is difficult to find oocytes on stage III and IV in experimental group for inhibiting the expression of steroidogenic factor protein, a large number of oocytes on stage V are accumulated, and many of them are becoming gray and broken. Therefore, the development of sexual organs of female GIFT is influenced through inhibiting the expression of steroidogenic factor protein, causing in the abnormal formation of primary sexual characteristics, and a large number of mature eggs cannot be excreted from the body, resulting in the eggs to be overmature and broken.

Detection of SF1 Protein Level:

The protein expression level of target genes in tilapia gonadal tissue was detected through western blot. 0.05 g of gonadal tissue sample was selected, the tissue was crushed with liquid nitrogen and a mortar, 1 mL of platelet aggregation buffer induced by Ristomycin (containing 1% 10 mg/mL Phenylmethanesulfonyl fluoride) was added, and the mixture was homogenated with Polytron homogenizer at 4° C. and 15000 g for 1 min. The protein supernatant was aspirated after being centrifuged at 4'C and 12000 g for 15 min. The supernatant was taken to measure the concentration of protein with the BCA protein assay kit (Sigma-Aldrich), then the final protein concentration in each sample was adjusted to 2 μg/μL. 20 μg of total protein in each sample was taken to prepare for SDS-PAGE electrophoresis. 6×sodium dodecyl sulfate (SDS) protein loading buffer was added. The protein was denatured by heating at 100° C. for 10 min, and was separated through SDS polyacrylamide gel electrophoresis (SDS-PAGE), and then the protein was transferred onto a polyvinylidene fluoride membrane using a wet transfer method.

The membrane was blocked in 5% (w/v) skimmed milk for 3 hours, washed with TBST, and then the membrane was incubated with the main target gene antibody at 4° C. overnight. The next day, the membrane was washed with TBST and incubated with the corresponding second antibody (rabbit IgG) for 1 h at room temperature. The protein on the membrane was colored by using ECL and western blot system. Glyceraldehyde-3-phosphate dehydrogenase (GAPDH) was taken as an internal reference protein. Before the formal experiment, the marker of the target protein was analyzed to detect the target band.

In the protein sequences translated by SF1-1 and SF1-2, only a few proteins at the N-terminal are different; meanwhile, this differential fragment is not suitable for antibody design after analysis. Therefore, SF1-1 and SF1-2 could only share one antibody for detection in this experiment, which cannot be clearly distinguished.

Figure 11:
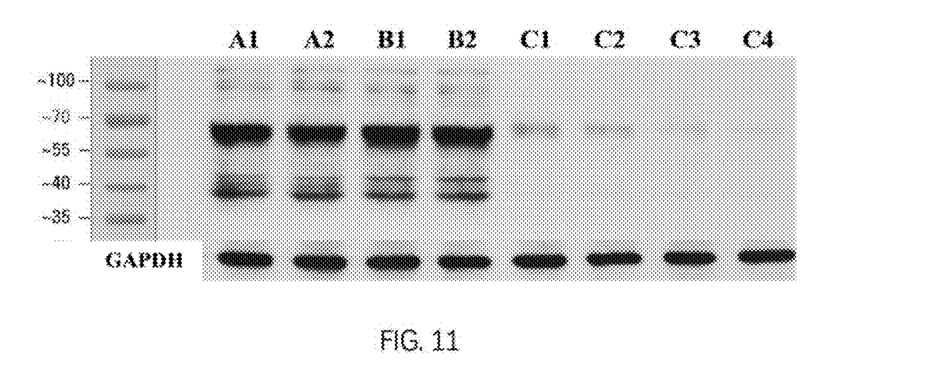
FIG. 11 shows the protein expression level of steroidogenic factor 1 in gonad tissue of male fish in each experimental group, wherein A1 and A2 are male fish in control group; B1 and B2 are negative control groups. C1, C2, C3 and C4 are male fish in experimental groups; GAPDH is the internal reference in each experimental group.
Figure 12:
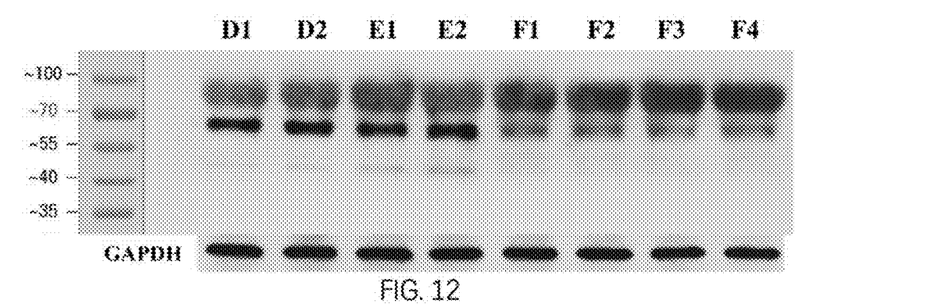
FIG. 12 shows the protein expression level of steroidogenic factor 1 in gonad tissue of female fish in each experimental group, wherein D1 and D2 are female fish in control group; E1 and E2 are negative control groups. F1, F2, F3 and F4 are female fish in experimental groups; GAPDH is the internal reference in each experimental group.

It can be seen from FIG. 11 and FIG. 12 that the protein expression level of steroidogenic factor 1 is significantly inhibited after the antisense RNA sequence is introduced into male and female GIFT.

It can be seen from the above examples that the antisense RNA sequence of steroidogenic factor 1 was used for the first time to inhibit the expression levels of steroidogenic factor 1 gene mRNA and protein in the present application, which interfered the development of the gonads of female and male fish, especially male fish, causing insufficient secretion of estrogen and androgen, leading to degeneration of the sexual organs on male and female fish. The method of the application has the advantages of simple operation, minimal egg damage, high success rate, stable phenotype after breeding, and excellent application prospects.

The above described are only preferred embodiments of the present application, it should be understood by those skilled in the art that, without departing from the principle of the present application, several improvements and modifications can be made, and these improvements and modifications also should be regarded as the protection scope of the present application fall into the scope of the present application.

What is claimed is:

1. A combination of antisense RNA sequences, wherein the combination of antisense RNA sequences comprises antisense RNA of steroidogenic factors SF1-1 and SF1-2, the antisense RNA of steroidogenic factor SF1-1 comprises an Anti-SF1-1-I and an Anti-SF1-1-II; the antisense RNA of steroidogenic factor SF1-2 comprises an Anti-SF1-2-I and an Anti-SF1-2-II; the nucleotide sequences of the Anti-SF1-1-I, the Anti-SF1-1-II, the Anti-SF1-2-I and the Anti-SF1-2-II are set forth in SEQ ID NO:1-SEQ ID NO:4 respectively.

2. A method for producing tilapia with degenerated sexual organs by using the combination of antisense RNA sequences in claim 1 to regulate the expression of SF1-1 and SF1-2 within tilapia.

3. The method according to claim 2, comprising the steps of:

1) cloning the Anti-SF1-1-I of SEQ ID NO: 1 into a first expression vector to obtain a first recombinant vector;
cloning the Anti-SF1-1-II of SEQ ID NO: 2 into a second expression vector to obtain a second recombinant vector;
cloning the Anti-SF1-2-I of SEQ ID NO: 3 into a third expression vector to obtain a third recombinant vector; and
cloning the Anti-SF1-2-II of SEQ ID NO: 4 into a fourth expression vector to obtain a fourth recombinant vector;

2) using the first recombinant vector, the second recombinant vector, the third recombinant vector, and the fourth recombinant vector as templates respectively, and performing PCR amplification with specific primers to obtain four amplified products;
3) mixing the four amplified products of step 2) to obtain a product mixture, mixing the product mixture with a cationic liposome and a spermatozoa preservative fluid, and equilibrating at 15-30° C. for 20-40 minutes to obtain transfection reagents;
4) mixing the transfection reagents with eggs for transfection to obtain transfected eggs; and
5) mixing the transfected eggs with sperms for fertilization and hatching to obtain tilapia fries with degenerated sexual organs.

4. The method according to claim 3, wherein the expression vector in step 1) is a pcDNA3.1 expression vector, and the site of the cloning is located between the Xho I and Xba I restriction sites.

5. The method according to claim 3, wherein the specific primers in step 2) comprises PolyAF2 and PolyAR1, and the nucleotide sequences of the PolyAF2 and the PolyAR1 are set forth in SEQ ID NO:5 and SEQ ID NO:6.

6. The method according to claim 3, wherein the volume ratio of the four amplified products in step 3) is (0.5-1.5):(0.5-1.5):(0.5-1.5):(0.5-1.5); the volume ratio of the total volume containing the four amplified products, the cationic liposome and the spermatozoa preservative fluid is 4:4:(60-65).

7. The method according to claim 3, wherein the spermatozoa preservative fluid comprises the following components: 3%-5% sucrose in mass fraction, 2%-4% glycerol in volume fraction, and 0.5%-1.5% DMSO in volume fraction, with water as a solvent.

8. The method according to claim 3, wherein a solution for promoting the opening of the fertilization hole is added to the eggs in step 4), wherein the solution for promoting the opening of the fertilization hole comprises the following components: sodium chloride 5-7 g/L, potassium chloride 0.05-0.15 g/L, calcium chloride 0.05-0.15 g/L, sodium bicarbonate 0.05-0.15 g/L, sodium dihydrogen phosphate 0.05-0.15 g/L and glucose 1.0-1.5 g/L, with water as a solvent.

9. The method according to claim 8, wherein 1.5 mL of the solution for promoting the opening of the fertilization hole and 0.8 mL of transfection reagent are added to every 120 to 150 eggs.

* * * * *

SEQUENCE LISTING

<160> NUMBER OF SEQ ID NOS: 12

<210> SEQ ID NO 1
<211> LENGTH: 113
<212> TYPE: DNA
<213> ORGANISM: Artificial Sequence
<220> FEATURE:
<223> OTHER INFORMATION: Anti-SF1-1-I

<400> SEQUENCE: 1
catctggttc agtcactttg cgtaagctga cgtcgttcat gaacctacag acacatacgg    60
cggttgagtg atttattatc ctgcgatatg tttactttta gatttttatt ttt          113

```
<210> SEQ ID NO 2
<211> LENGTH: 104
<212> TYPE: DNA
<213> ORGANISM: Artificial Sequence
<220> FEATURE:
<223> OTHER INFORMATION: Anti-SF1-1-II

<400> SEQUENCE: 2
aataactgac aaactattct taacaatgaa atgtgtttat agtttgttgt tgtggttttg      60
ttgctttcac ctgatctgac tcgctgctga gtctcatctg gttc                     104

<210> SEQ ID NO 3
<211> LENGTH: 102
<212> TYPE: DNA
<213> ORGANISM: Artificial Sequence
<220> FEATURE:
<223> OTHER INFORMATION: Anti-SF1-2-I

<400> SEQUENCE: 3
tgctgtctat atcggggatg ctttaggagc cagaagggcc aatagaaagt gtagtacgat      60
gatgaccatt caagagctca gagtgaaact cctttccttc gc                        102

<210> SEQ ID NO 4
<211> LENGTH: 102
<212> TYPE: DNA
<213> ORGANISM: Artificial Sequence
<220> FEATURE:
<223> OTHER INFORMATION: Anti-SF1-2-II

<400> SEQUENCE: 4
aggaaaacgg aggcacttac cgtgagcctt gtctcccaac atttgagcag cagacagcag      60
gcaggcagtg atgattgtct gatgattaaa acctggatgt ag                        102

<210> SEQ ID NO 5
<211> LENGTH: 23
<212> TYPE: DNA
<213> ORGANISM: Artificial Sequence
<220> FEATURE:
<223> OTHER INFORMATION: PolyAF2

<400> SEQUENCE: 5
ttttgcgctg cttcgcgatg tac                                             23

<210> SEQ ID NO 6
<211> LENGTH: 22
<212> TYPE: DNA
<213> ORGANISM: Artificial Sequence
<220> FEATURE:
<223> OTHER INFORMATION: polyAR1

<400> SEQUENCE: 6
tccccaatcc tccccttgc tg                                               22

<210> SEQ ID NO 7
<211> LENGTH: 20
<212> TYPE: DNA
<213> ORGANISM: Artificial Sequence
<220> FEATURE:
<223> OTHER INFORMATION: SF1-1-F

<400> SEQUENCE: 7
tgtgctcacc ggtagtttgg                                                 20
```

```
<210> SEQ ID NO 8
<211> LENGTH: 20
<212> TYPE: DNA
<213> ORGANISM: Artificial Sequence
<220> FEATURE:
<223> OTHER INFORMATION: SF1-1-R

<400> SEQUENCE: 8
atgggcagct ctgtggaatg                                              20

<210> SEQ ID NO 9
<211> LENGTH: 20
<212> TYPE: DNA
<213> ORGANISM: Artificial Sequence
<220> FEATURE:
<223> OTHER INFORMATION: SF1-2-F

<400> SEQUENCE: 9
gagcgaagga aaggagtttc                                              20

<210> SEQ ID NO 10
<211> LENGTH: 20
<212> TYPE: DNA
<213> ORGANISM: Artificial Sequence
<220> FEATURE:
<223> OTHER INFORMATION: SF1-2-R

<400> SEQUENCE: 10
tgactcgctg ctgagtctca                                              20

<210> SEQ ID NO 11
<211> LENGTH: 20
<212> TYPE: DNA
<213> ORGANISM: Artificial Sequence
<220> FEATURE:
<223> OTHER INFORMATION: 18S rRNA-F

<400> SEQUENCE: 11
ggccgttctt agttggtgga                                              20

<210> SEQ ID NO 12
<211> LENGTH: 20
<212> TYPE: DNA
<213> ORGANISM: Artificial Sequence
<220> FEATURE:
<223> OTHER INFORMATION: 18S rRNA-R

<400> SEQUENCE: 12
ttgctcaatc tcgtgtggct                                              20
```